United States Patent [19]

Narang

[11] Patent Number: 5,618,673
[45] Date of Patent: Apr. 8, 1997

[54] OLIGONUCLEOTIDES AND THEIR USE IN AN ASSAY FOR ENCEPHALOPATHIES

[75] Inventor: Harash K. Narang, Newcastle-upon-Tyne, England

[73] Assignee: British Technology Group Limited, London, England

[21] Appl. No.: 476,614

[22] Filed: Jun. 7, 1995

Related U.S. Application Data

[63] Continuation of Ser. No. 196,156, filed as PCT/GB92/01426, Aug. 3, 1992, abandoned.

[30] Foreign Application Priority Data

Aug. 20, 1991 [GB] United Kingdom .................. 9117910

[51] Int. Cl.$^6$ .................. C07H 21/02; C07H 21/04; C12P 19/34; C12Q 1/68; C12Q 1/70
[52] U.S. Cl. .................. 435/6; 435/5; 435/91.2; 435/810; 536/22.1; 536/23.72; 536/24.3; 536/24.33
[58] Field of Search .................. 435/6, 5, 91.2, 435/810; 536/22.1, 23.72, 24.3, 24.33; 935/77, 78

[56] References Cited

U.S. PATENT DOCUMENTS 4,683,195  7/1987  Mullis et al. .................. 435/6

FOREIGN PATENT DOCUMENTS 327377     8/1989   European Pat. Off. .
8911545    11/1989  WIPO .
WO93/11155 6/1993   WIPO .

OTHER PUBLICATIONS

N. Hunter, "Scrapie and GSS—the importance of protein", TINS, 14, (No. 9), 389–390 (1991).
S. B. Prusiner, M. Torcha & D. Westaway, "Molecular Biology and Genetics of Prions", Cornell Veterinarian, 81 (No. 2), 85–101 (1991).
Duguid et al., P.N.A.S. 85: 5738–5742, 1988.
Locht et al., P.N.A.S. 83: 6732–6736, 1986.
Goldmann et al., J. Gen. Virology 72(1): 201–204, 1991.
H.K. Narang et al., "Increased multimeric mitochondrial DNA in the brain of scrapie–infected hamsters", Intervirology 32, 316–324 (1991).
H.K. Narang, D.M. Asher and D.C. Gajdusek, "Evidence that DNA is present in abnormal tubulofilamentous structures found in scrapie", Proc. Natl. Acad. Sci. USA 85, 3575–3579 (1988).
H.K. Narang, D.M. Asher and D.C. Gajdusek, "Tubulofilaments in negatively stained scrapie–infected brains . . . ", Proc. Natl. Acad. Sci. USA 84, 7730–7734 (1987).
H.K. Narang, "Evidence of ssDNA in tubulofilamentous particles . . . " Intervirology 32, 185–192 (1991).
J.M. Aiken and R.F. Marsh, "The Search for Scrapie Agent Nucleic Acid", Microbiol Rev. 54 (3), 242–246 (1990).
N. Meyer et al., "Search for a putative scrapie genome in purified prion fractions reveals a paucity of nucleic acids", J. Gen. Virol. 72, 37–49 (1991).
H.K. Narang and R.H. Perry, "Diagnosis of Creuzfeldt–Jakob disease by electron microscopy", The Lancet 335, 663–664 (Mar. 17, 1990).
H. Sorum et al., "An oligonucleotide probe used to detect scrapie infected sheep", Abstracts of the American Society of Microbiologists, 363 Abstract No. C–188 (1988).
"The Guardian" (English newspaper), Apr. 27, 1991.
"The Guardian" (English newspaper), Jun. 22, 1991.
"The Guardian" (English newspaper), Aug. 16, 1991.
C. Locht et al., "Molecular cloning and complete sequence of prion protein cDNA from mouse brain infected with the scrapie agent", Proc. Natl. Acad. Sci. USA 83, 6372–6376 (1986).

(List continued on next page.)

*Primary Examiner*—Stephanie W. Zitomer
*Assistant Examiner*—Paul B. Tran
*Attorney, Agent, or Firm*—Nixon & Vanderhye

[57] ABSTRACT

Oligonucleotides of formula $$(X)_a\text{-}(6N\text{-palindrome})_n\text{-}(Y)_b \qquad (1)$$

wherein:

"6N-palindrome" represents TACGTA, ACGTAT, CGTATA, GTATAC, TATACG or ATACGT (read in the conventional notation with the 5'-end at the left);

n is an appropriate integer of at least 2;

X is a length of appropriate 5'-end or tailing DNA and a is 0 or 1; and

Y is a length of appropriate 3'-end or heading DNA and b is 0 or 1;

or any labelled form thereof or any derivative thereof which retains the ability of the 6N-palindrome sequence to anneal or hybridize to its complementary sequence are useful in assay of encephalopathies such as scrapie, BSE or CJD. Preferably they are used as PCR primers to amplify DNA in the sample. PCR product can be detected by restriction with an appropriate enzyme and comparing the restricted and unrestricted products.

58 Claims, No Drawings

OTHER PUBLICATIONS

P.R. Wills and A.J. Hughes, "Stem loops in HIV and Prion Protein mRNAs", Journal of Acquired Immune Deficiency Syndrome 3, 95–97 (1990).

W. Goldmann et al., "Different forms of the bovine PrP gene have five or six copies of a short, G–C–rich element within the protein–coding exon", J. Gen. Virology 72 (1), 201–204 (Jan. 1991).

D. Westaway et al., "Unraveling prion diseases through molecular genetics", TINS 12, (6), 221–227 (1989).

N. Hunter et al., "Linkage of the Scrapie–associated fibril protein (PrP) Gene and Sinc . . . ", J. Gen. Virology 68, 2711–2716 (1987).

G.A Carbon et al., "Linkage of Prion Protein and Scrapie Incubation Time Genes", Cell 46, 503–511 (1986).

R.H. Boerman et al., "Diagnosis of progressive multifocal encephalopathy by hybridisation techniques", J. Clin. Path 42, 153–161 (1989).

Y. Furuta et al., "In situ hybridisation with digoxigenin–labelled DNA probes . . . ", J. Clin. Path., 42, 153–161 (1989).

C. Bellinger–Kawahara et al., "Purified scrapie prions resist inactivation by UV irradiation", J. Virology 61, 159–166 (1987).

C. Bellinger–Kawahara et al., "Purified scrapie prions resist inactivation by procedures . . . ", Virology 160, 271–274 (1987).

R. Gabizon et al., "Purified prion proteins and scrapie infectivity copartition into liposomes", Proc. Natl. Acad. Sci. 84, 4017–4021 (1987).

J.R. Duguid, R.G. Rohwer and B. Seed, "Isolation of cDNAs of scrapie–modulated RNAs . . . ", Proc. Natl. Acad. Sci. USA 85, 5738–5742 (1988).

Annual Report of the UK Agricultural and Food Research Council, 20–22 and 72 (1990).

C. Weissmann, "A unified theory of prion propagation", Nature 352, 679–683 (Aug. 1991).

M. Salvatore et al., "Nuclease and protease resistance of the 263K scrapie agent does not depend on the presence of PrP protein", Abstracts of the IVth European Meeting of Neuropathology, Clin. Neuropath. 11, 231–232 (1992).

B.E. Griffin, "Camouflaged DNA" Nature 354, 25–26 (Nov. 1991).

K. Carr, "A question of conformation" Nature 365, 386 (1993).

M. Moser et al., "An anti–prion protein", Nature 362, 213–214 (1993).

OLIGONUCLEOTIDES AND THEIR USE IN AN ASSAY FOR ENCEPHALOPATHIES

This is a continuation of application Ser. No. 08/196,156, filed as PCT/GB92/01426 Aug. 3, 1992, now abandoned.

BACKGROUND OF THE INVENTION

1. Field of the invention

This invention is in the field of assay of encephalopathies in humans and animals. The term "encephalopathy" is used herein to refer to neurodegenerative diseases implicating prions such as scrapie, in sheep and goats, bovine spongiform encephalopathy (BSE) in cattle, mink and cats and Creutzfeld-Jakob Disease (CJD), Gerstmann-Straüssler-Scheinker Syndrome (GSS) and kuru in humans. The term "assay" is used herein to cover mere detection (the likely ordinary use envisaged) and a quantitative or semi-quantitative procedure in which some estimate is made of the amount of the DNA present in the sample.

2. Description of the related art

The state of knowledge of the causative agent of encaphalopathies has been summarised recently by N. Hunter, TINS 14 (9), 389–390 (1991) and by S. B. Prusiner, M. Torcha and D. Nestaway, Cornell Veterinarian 81 (2), 85–101 (1991).

The infectious agent is a particle which differs from a virion and has been termed a "prion". Prions are thought to contain little or no nucleic acid and are composed largely of protease-resistant protein (PrP), which is encoded by a cellular gene of the host. This feature distinguishes prions sharply from virions. To date, no prion-specific nucleic acid has been identified which is required for transmission of disease.

Virus-like tubulofilamentous particles 23–26 nm in diameter have been seen consistently in the brains of all known spongiform encephalopathies. These particles have been investigated by H. K. Narang, Intervirology 32, 185–192 (1991) and H. K. Narang, D. M. Asher and D. C. Gajdusek, Proc. Natl. Acad. Sci. USA 85, 3575–3579 (1988) and 84, 7730–7734 (1987). They have a core of prions in a rod-like form. The prion rods are also termed scrapie-associated fibrils (SAF). Over the core is a layer of DNA, removable by DNAse and above that lies an outer protein coat which is digestible by a protease. In the Intervirology paper it is noted that no evidence as yet supports the existence of scrapie-specific nucleic acid, but it will be important to purify tubulofilamentous particles in order to characterise the nucleic acid and determine its relationship to the disease. Very recently H. K. Narang, N. S. Millar, D. M. Asher and D. C. Gajdusek, Intervirology 32, 316–324 (1991), have reported an increase in multimeric mitochondrial DNA in the brain of scrapie-infected hamsters, but, again, stated that there was no evidence for a scrapie-specific nucleic acid.

In their review entitled "The Search for Scrapie Agent Nucleic Acid", J. M. Aiken and R. F. Marsh, Microbiol. Rev. 54 (3) 242–246 (1990), concluded that the lack of success in identifying a scrapie-specific nucleic acid suggests that if there is such a nucleic acid, it would appear to be a very rare, or very small RNA or an RNA or DNA species having significant sequence similarity to nucleic acids present in uninfected tissue. Similarly, N. Meyer, V. Rosenbaum, B. Schmidt, K. Gilles, C. Miranda, D. Groth, S. B. Prusiner and D. Riesner, "Search for a putative scrapie genome in purified prion fractions reveals a paucity of nucleic acids", J. Gen. Virol. 72, 37–49 (1991) noted that prions resist inactivation by harsh procedures that specifically hydrolyse or modify nucleic acids, a feature which argues that they are probably devoid of polynucleotides, but that such negative results are always vulnerable to the criticism that a putative scrapie-specific nucleic acid might be so well protected by some unusual structure that its presence is yet to be detected. These authors concluded that the nucleic acid would have to be very small (of size less than 100 nucleotides), very efficient or heterogeneous in size.

The most reliable method of detecting an encephalopathy is histologically, especially by electron microscopy. See H. K. Narang and R. H. Perry, The Lancet, 335, 663–664 (March 17, 1990), and H. K. Narang, D. M. Asher and D. C. Gajdusek, Proc. Natl. Acad. Sci. USA 84, 7730–7734 (1987), but this requires brain tissue and is a slow and painstaking method.

It would be desirable to have a method of diagnosis based on nucleic acid identification. Such methods have been suggested. See H. Sorum, B. Hyllseth, R. Krona and O. Olsvik, Abstracts of the Annual Meeting of the American Society of Microbiologists 1988, page 363, Abstract No. C-188, who used a probe of DNA derived from the gene sequence coding for prion protein. Since, however, it is well known that prion protein is encoded by a normal chromosomal gene found in all mammals, including those affected by encephalopathies, the above-cited work has not gained acceptance. PCT Patent Application Publication No. WO89/11545 (Institute for Animal Health Ltd.) purports to describe a method of detection of scrapie by use of a restriction fragment length polymorphism (RFLP) linked to the so-called Sinc gene associated with short incubation times of sheep infected by scrapie. The RFLP is said to be located in a non-coding portion associated with the gene for prions. At best, this method would detect only sheep with the short incubation time characteristic. Hitherto, methods of diagnosis based on nucleic acid identification have not been successful or even likely to be successful, since an encephalopathy specific nucleic acid has eluded detection despite numerous attempts.

Several press articles in 1991 in the English newspaper "The Guardian" (27 April, 22 June, 16 August) report that the present inventor believes that he has found the genetic fingerprint for BSE and related diseases. No further information about the nature of the genetic fingerprint is given.

SUMMARY OF THE INVENTION

By a remarkable piece of research, the present inventor has found a scrapie-specific nucleic acid, which is also believed to be specific for other encephalopathies. The apparently unique nature of this nucleic acid forms the basis of a method of diagnosis which typically involves either (a) using a sequence from it as the basis of a DNA amplification, especially polymerase chain reaction (PCR), primer to make a sufficient amount of it for detection by a restriction fragment length method or (b) labelling it and using it as an oligonucleotide probe in a sensitive assay which includes a step of hybridising the probe to nucleic acid of the sample. The assay can be carried out on body fluids.

The scrapie-specific nucleic acid is single-stranded DNA and includes the sequence $(TACGTA)_n$ where n is at least 6. The basic six nucleotide unit of this repeat sequence is palindromic, in the sense that a complementary DNA would have the same TACGTA sequence when read in the 5' to 3' direction. The full length sequence of the DNA is not yet known, but it is suspected that n is very much larger than 6, perhaps of the order of 20–30 and further that the DNA is probably of the general form:

$$(TACGTA)_{n_1}\text{-}L_1\text{-}(TACGTA)_{n_2}\text{-}L_2\text{-}(TACGTA)_{n_3}\text{-}L_3 \ldots$$

wherein $n_1, n_2, n_3 \ldots$ is a series of integers which may be the same or different and $L_1, L_2, L_3 \ldots$ is a series of linking lengths of DNA which may be the same or different. The general form shown might be headed at the 3'-end and/or tailed at the 5'-end by other DNA, of unknown sequence. The number of $(TACGTA)_n$ blocks, i.e. the extent of the series $n_1, n_2, n_3 \ldots$, is not yet known, nor is therefore the number of linkers $L_1, L_2, L_3 \ldots$. Nevertheless, it is already apparent that the TACGTA sequence is valuable In diagnosis. A search has shown it to be known in the form TACGTA unrepeated, i.e. n=1, in 93 genes, the double sequence $(TACGTA)_2$, i.e. n=2, in certain Drosophila and yeast genes, but higher repeats, i.e. n=3 or more, are believed unique.

The present invention provides oligonucleotides of formula $$(X)_a\text{-}(6N\text{-palindrome})_n\text{-}(Y)_b \quad (1)$$

wherein:

"6N-palindrome" represents TACGTA, ACGTAT, CGTATA, GTATAC, TATACG or ATACGT (i.e. the palindromic sequence beginning at any one of the six nucleotides thereof), n is an appropriate integer of at least 2; X is a length of appropriate 5'-end or heading DNA and a is 0 (i.e. no heading DNA is present) or 1; and Y is a length of appropriate 3'-end or tailing DNA and b is 0 (i.e. no tailing DNA is present) or 1: or any labelled form thereof or derivative thereof which retains the ability of the 6N-palindrome sequence to anneal or hybridise to its complementary sequence). "Appropriate" means compatible with possible use of the oligonucleotide as a DNA amplification, e.g. PCR, primer or in hybridisation, e.g. as a labelled probe. There are, of course, practical limits to the length of the oligonucleotide depending on its intended use. For use as a primer n is normally 2, 3 or 4. For use as a probe the length will not normally exceed 200 nucleotides, preferably not more than 70, in all. The term "label" refers to any detectable substance or residue of a substance. The term "oligonucleotide" excludes complete genes or copies of genes or of complete cDNA complementary to complete mRNA transcribed from genes.

The invention includes the above-defined oligonucleotides both per se and for any use in or relating to assay of an encephalopathy.

In a third aspect, the invention includes a kit for carrying out a polymerase chain reaction, the kit comprising, i.e. consisting of or including, (1) deoxyribonucleotides, (2) a polymerase suitable for the PCR and (3) at least one oligonucleotide of the invention as defined above, as a primer. Such kit components are normally provided within separate containers which together form the kit or part of the kit.

Fourthly, the invention includes specifically a method of assay for an encephalopathy, which comprises treating a sample suspected of containing DNA specific for the encephalopathy to amplify the DNA, for example by the PCR, detecting the product of the amplification and thereafter analysing the product for the presence of multiple copies of the TACGTA repeat sequence, especially by restricting the product enzymically and comparing the restricted product with unrestricted product.

Fifthly, the invention includes specifically a method of assay for an encephalopathy which comprises probing a sample suspected of containing DNA specific for an encephalopathy, optimally after amplification of the DNA, with a labelled complementary probe DNA, under appropriate hybridisation conditions and assaying the hybrid product thus obtained. It is envisaged that the complementary DNA would normally comprise a $(6N\text{-palindrome})_n$ sequence, although it cannot be excluded that it could alternatively comprise linking sequence $(L_1, L_2, L_3)$ or some part thereof. Such a linking sequence could be of formula $(A)p(TA)q(T)r$ where p is 0 or 1 and q Is a number from 1 to 20, especially from 3 to 9 and r is 0 or 1. Of course, it could comprise both types of sequence.

Sixthly, the invention further includes scrapie-specific DNA which comprises at least one sequence of formula $(TACGTA)_n$ where n is at least 6. It may optionally have other components of sequence, as indicated above.

DESCRIPTION OF THE PREFERRED EMBODIMENTS (a) The oligonucleotides

Although the invention includes the oligonucleotides per se, the definition of their preferred features pays attention to their chief presently contemplated use, namely as DNA amplification primers. For this purpose n in formula (1) is preferably 2, 3 or 4 and the minimum preferred length of palindromic sequence is about 12. The term "palindromic sequence" herein means any six or more consecutive nucleotides selected from SEQ ID NO: 1:
1 TACGTATACG TA 12, which can be written as $(TACGTA)_2$. In other words, it includes palindromic sequence within "(6N-palindrome)" units and within "(X)" and "(Y)" of formula (1). Less than the preferred minimum of 12 might result in an ability to detect DNA having only one TACGTA block, which is not too uncommon, but this might be tolerable in some circumstances, e.g. where more than one detection method is being used. Even with 12 bases, e.g. $(TACGTA)_2$, there is some possibility of detecting a twice-repeated sequence in a yeast, although there could be further circumstances in which this possibility could be well tolerated. A more preferred length of palindromic sequence is from 12 to 24, specially 16 to 24, and most especially 17 or 18. A palindromic sequence longer than 24, e.g. $(TACGTA)_4 TA$, could be tolerable in some circumstances, but there would probably be a self annealing problem. That is to say, the 3'-end of the primer could anneal to its own 5'-end instead of to the encephalopathy-specific DNA of the sample. Indeed, it is this very capacity for self-annealing, scrapie-specific DNA, which probably explains why the DNA has evaded detection previously.

The oligonucleotides could be modified in various ways, starting from the fundamental repeated palindromic sequence, to serve as primers. Extension of the primer proceeds from the 3'-end. Therefore, primers could have an "irrelevant" 5'-tail, for example of formula $(N)_m$ where N is any single nucleotide, e.g. A, C, G or T, and m is sufficiently large to create a poly-N tail of very low probability of occurrence in natural sequences, e.g. 8 or more, especially 10 or more. Preferably, however, a 5'-tail consists of or includes the sequence $(A)p(TA)q$ where p is 0 or 1 and q is at least 1, especially from 1 to 3, immediately to the 5'-end of $(TACGTA)_n$. There is no definite upper limit to the length of the 5'-tail, but if it is too long it is likely to interfere with the PCR. Tails of moderate length have been previously proposed for PCR primers, principally as a means of linking them to an insoluble support, see e.g. U. K. Patent Specification 2233654A (NRDC). Such a tail is not necessarily composed entirely of nucleic acid.

Formula (1) above allows for the possibility that the primers will not consist of palindromic sequence in an exact whole number of repeats, e.g. consist of $(TACGTA)_n$ with no other nucleotides at either end. Thus, the head and/or tail elements can comprise residues of palindromic sequence, arranged, of course, in the same order as in the repeat palindromic sequence. For example, a 17-mer primer could have the SEQ ID NO: 2:

1 ATACGTATAC GTATACG 17 which is of formula (1) wherein "6N-palindrome" is TATACG, n is 2, a is 0, b is 1 and the 5'-tail is ATACG.

Ordinarily, for use in the PCR, b will be 0, as it is not desirable to have any nucleotides ahead of the 3'-end of the palindromic sequence, as they would inhibit primer extension. However, the mismatch of a single nucleotide might be tolerable, e.g. in the 18-met SEQ ID NO: 3:

1 TATACGTATA CGTATACH 18 where nucleotide H at the 3'-end is A, C or T and therefore not a residue of the palindrome (G is required for the palindrome).

When the oligonucleotide is intended to be used in a method of assay involving a hybridisation step, It can also consist entirely of palindromic sequence or also contain non-palindromic nucleotides to the 5'-or 3'-end or both of the palindromic sequence. Such non-palindromic sequence could be any unlikely to interfere with the assay. For example, it could consist of or include a sequence (A)p(TA)q, as mentioned above, at the 5'-end or, complementarily, 3'- (T)p(AT)q 5' at the 3'-end of a sequence 3' ATGCAT 5'.

For use in the PCR reaction the oligonucleotide will not ordinarily be labelled except possibly at its 5'-end, see e.g. A.-C. Syvänen, M. Bengström, J. Tenhunen and H. Söderlund, Nucleic Acids Research 16, 11327–11338 (1988). In principle, it could be labelled in any other way which does not interfere with annealing or primer extension, if so desired. For use in an assay which involves hybridisation, the oligonucleotide will normally be used in a labelled form, labelling being by any appropriate method such as radiolabelling, e.g. by $^{32}P$, $^{35}S$ or by biotinylation (which can be followed by reaction with labelled avidin or streptavidin). However, it is also possible to use an unlabelled oligonucleotide as a probe provided that it is subsequently linked to a label. For example, the oligonucleotide could be provided with a poly-C tail which could be linked subsequently to labelled poly-G.

The oligonucleotides of the invention will not ordinarily be longer than 200 nucleotides, even when used as probes, and in practice are likely to be very much shorter, especially up to 70 nucleotides and more especially up to 45 nucleotides long. Thus, especially for PCR purposes, they are unlikely to comprise more than 24 nucleotides of the palindrome plus an optional 5'-end or tail of (say) 8–20 nucleotides, making 32–44 nucleotides in all.

(b) The assay method

In the preferred method, the oligonucleotide is used to amplify the sample DNA. This is conveniently performed at present by the PCR, but, in principle, any other method could be used which involves using the oligonucleotide to prime the synthesis of or otherwise create a second strand of DNA using the single-stranded DNA of the sample as a template.

The PCR can be applied very easily by using a commercially available kit and an oligonucleotide of the invention as a primer. Because of the repetitive nature of the sequence of the DNA of the sample, the same oligonucleotide can be used as both a forward and reverse primer. Commercial kits normally consist of deoxynucleotides (A, C, G and T), a polymerase which will withstand the temperatures used in the PCR such as Taq polymerase, buffers and control DNA for testing the kit. Therefore, the oligonucleotide primer can be sold on its own for use with the kit. However, it is also possible to sell an add-on kit comprising at least one oligonucleotide primer of the invention, a restriction enzyme for cutting the palindromic sequence and optionally other components such as a length of control DNA similar to the encephalopathy-specific DNA, for testing the add-on kit.

The PCR conditions can be any known for use in this kind of assay, conveniently those recommended for use with the kit.

The PCR will yield a product in the form of DNA of varying lengths containing the palindromic sequence. This can be analysed in any desired way, but a method relying on restriction by an enzyme is probably the easiest. The PCR product will yield bands of various molecular weights. In some instances the encephalopathy-specific DNA will be primed near its 3'-end, which will generate multiple copies of large molecules. The PCR product is divided into two portions. The first is run on a resolving gel to show a band Of high molecular weight associated with the encaphalopathy-specific DNA. The second portion is restricted with a restriction enzyme which cuts the palindromic sequence. This will severely reduce the length of the longer DNA and eliminate certain other bands of shorter DNA altogether. Multiple restrictions of TACGTA will produce many bands of too low a molecular weight to be detected. By comparing the restriction fragment length patterns obtained from the two portions, it can readily be determined whether the encephalopathy-specific DNA is present in the sample.

Examples of suitable enzymes are SnaBI and AccI which cut between the C and G of TACGTA and MaeI and SnaI which cut between the A and T, i.e. between one TACGTA sequence and the next. All these enzymes leave blunt ends and all recognise the six-base sequence.

In the alternative, hybridisation, method, the sample DNA could be first amplified, e.g. by a PCR method, or used as it is. A hybridisation probe is preferably from 16 to 100 nucleotides, especially from 16 to 45 long. The hybridisation assay can be carried out in any of the conventional ways. Southern blotting will probably be very convenient.

(c) The samples

The invention can be applied to assay of samples from any body tissue or fluid in which the infectious agent and therefore the encephalopathy-specific DNA is likely to be present in a reasonable concentration, especially in whole blood, serum, plasma, cerebrospinal fluid, saliva, kidney, spleen, liver, and placenta. Brain and spinal cord could be used if desired.

(d) The encephalopathies

Although the invention has been pioneered using the DNA from the infectious particles of scrapie, current opinion is that BSE, scrapie, CJD and other encephalopathies probably result from the same infectious agent, transferred to another species. If it is not precisely the same, then it is probably very similar. It is therefore believed that the TACGTA palindromic sequence appears in all the known encephalopathies and possibly others. Accordingly, the sample can be taken from any animal, including those mentioned above, or human believed to be suffering from an encephalopathy.

The following Examples illustrate the invention.

EXAMPLE 1

Example 1 describes the isolation and partial sequencing of a scrapie-specific single-stranded DNA.

MATERIALS AND METHODS (a) Animals

A total of 200 weanling female Golden Syrian hamsters were inoculated intracerebrally with the 263K strain of scrapie agent using 0.03 ml of a 10% suspension of scrapie-infected hamster brain. Clinically ill animals (65–90 days post inoculation) and a similar number of control, age-matched hamsters were killed in batches of 20.

(b) Purification of nucleic acid

Isolation of DNA was carried out at 0°–4° C. (unless otherwise stated) in sterile solutions. The brains of the hamsters were removed and each brain was homogenised in 10 ml of 0.32M sucrose (0°–4° C.) containing 10 mM $MgCl_2$ in Griffith tubes. The homogenates were centrifuged at 0°–4° C., at 725×g for 10 min. to remove host nuclei. The supernatant at 0°–4° C. was further centrifuged at 40,000×g for 1 hour. The pellet from 20 brains was resuspended in 5 ml of 10 mM $MgCl_2$ in water at 0°–4° C. to which ribonuclease A (RNase) bovine pancreatic type III-A (Sigma), 20,000 units and deoxyribonuclease type 1 (DNase), (Sigma) 20,000 units were added. The mixture was incubated at 37° C., mixing every 15 min. After incubating for 1½ hours with the nucleases TE buffer (20 mM Tris, 5 mM EDTA, pH 8.5) was added to a final volume to 30 ml (0°–4° C.). The mixture was centrifuged (0°–4° C.) again at 40,000×g for 1 hour, the pellet resuspended in 5 ml Tris EDTA buffer (pH 8.5 at 0°–4° C.), 10 mg/ml proteinase K (Boehringer) added and incubated for 1½ hours at 42° C. mixing every 15 min. Sodium dodecyl sulphate (SDS) was added to give a final concentration of 0.5% and nucleic acid was extracted from the mixture using the phenol/chloroform extraction procedure (Sambrook, Fritsch & Maniatis, 1989). The nucleic acid was precipitated in ethanol and resuspended in 25 µl/per brain Tris EDTA buffer pH 7.4 (TE).

(c) Further purification of nucleic acid

500 µl aliquots (nucleic acid from 20 brains, in ten aliquots) of the resuspended nucleic acid were re-treated and incubated for one hour at 42° C. with 10 mg/ml proteinase K. The nucleic acid was re-extracted from the mixture using the above phenol/chloroform extraction procedure and precipitated in ethanol and resuspended in 500 µl TE buffer. The preparation was re-treated by incubating with 200 units RNase (heat inactivated for DNase) in 10 mM $MgCl_2$ buffer for one hour at 37° C. The nucleic acid was re-extracted from the mixture using the above phenol/chloroform extraction procedure and precipitated in ethanol so that each tube contained DNA from five brains.

For the alkaline gel, the nucleic acid was resuspended in 500 mM NaOH and incubated at 65° C. for 90 min. The DNA samples were loaded containing 6× alkaline loading buffer into the wells of the alkaline gel. 6× alkaline loading buffer consists of 300 mN NaOH, 6 mM EDTA, 18% Ficoll (Type 400; Pharmacia) in water, 0.15% bromocresol green and 0.25% xylene cyanol FF.

(d) Agarose gel electrophoresis

Nucleic acid was separated by electrophoresis in 1.0% agrose (BRL) on horizontal slabs in TAE buffer (40 mM Tris-acetate, pH 7.6, 1 mM EDTA). Gels were stained with ethidium bromide which was incorporated in the agarose gel at a concentration of 2 µg/ml. Gels were run at 75 mA constant current. Lambda DNA HindIII digest fragments and 1 kb size markers (BRL) were used.

(e) Alkaline agarose gel

To prepare alkaline agarose gel a known amount of agarose (BRL) in distilled water was melted and equilibrated at 50° C. and 3 M NaOH was added to give a final concentration of 50 mM NaOH, 2 mM EDTA. When purification of the band was required from the gel, low melting agarose (BRL) was used. To prepare this gel, first a normal agarose bed was made with 1% agarose and, after the gel had set, the low-melting alkaline gel was poured on top as usual. It would normally be considered ridiculous to add ethidium bromide to an alkaline agarose gel for resolution of DNA. The ethidium bromide staining agent works by intercalating between strands of double-stranded DNA, but on an alkaline gel, double-stranded DNA would become single-stranded. In this instance, it was added (2 µg/ml) into the alkaline gel by mistake. Electrophoresis was carried out in 50 mM NaOH alkaline electrophoresis buffer at 40 mA constant current as described in detail by M. N. McDonell, M. N. Simon and N. Studier, J. Mol. Biol. 110, 119–146, (1977).

(f) Purification of nucleic acid from the alkaline gel

After electrophoresis on alkaline low melting agarose gel, a discrete band of about 1.2 kb of nucleic acid remained stained with ethidium bromide, but only in the lane loaded with nucleic acid of the scrapie-infected material. This 1.2 kb band which remained stained under alkaline conditions was cut from the gel. The piece of gel was neutralised by several changes in 20 volumes of 1.5M NaCl and 1M Tris buffer (pH 7.6). The concentration of NaCl and Tris was gradually dropped to 10 mM each. Finally the gel slice was weighed in a 1.5 ml micro-centrifuge tube and 3 volumes of distilled water added. The tube was incubated in a water bath at 60° C. for 5 min until the agarose had melted. Various unsuccessful attempts were made to further purify the nucleic acid. Best results were obtained without any further purification of this DNA in low melting agarose suspension which was used for synthesis of the second strand of cDNA. Various methods and combinations including the self-priming method by Klenow fragment of *E. coli* DNA Polymerase, to link synthetic DNA Linkers with terminal transferase were tried. An attempt was also made to link the scrapie-specific single-stranded DNA by terminal transferase to the plasmid DNA. All these methods used are described in detail in "Molecular Cloning, a Laboratory Manual", 2nd ed., J. Sambrook, E. F. Fritsch and T. Maniatis, Cold Spring Harbor Laboratory Press, 1989. The only method which was successful is described below.

10 µl suspension of the purified DNA in water from low melting agarose, 1 µl of synthetic random 14-mer oligonucleotide primer NEP-112X (Du Pont) in Taq Polymerase buffer was heated at 95°–100° C. for 5 min. The tube was allowed to cool slowly to 37° C., the resulting condensation was centrifuged and the tubes re-heated and cooled slowly to 37° C. twice, (with buffer only). 2 µl of 0.5 mM dNTPs mixture and one unit of AmpliTaq DNA Polymerase (Perkin Elmer Cetus) was added. The mixture was heated for three min at 80° C. and then at 75° C. for 5 min. An additional unit of AmpliTaq DNA Polymerase was added and temperature was gradually dropped, to 70° C. and then to 65° C., 60° C., 55° C. and 50° C., holding each temperature for 5 min. No PCR was carried out at this stage. The double-stranded DNA synthesised was again purified by phenol/chloroform extraction and ethanol-precipitated. The pellet was resuspended in 20 µl of distilled water and treated with 5 units of $S_1$ nuclease (Pharmacia) for 15 min at 37° C. and again purified by phenol/chloroform extraction method and ethanol-precipitated.

(g) Construction of a recombinant plasmid

The cDNA synthesised was ligated into M13mp10, Sma 1 cut and dephosphorylated (Amersham), with T4 DNA ligase. The recombinant phage was transformed into the competent *E. coli* strain DH5a (BRL) and plated on LB agar plates incubated overnight at 37° C. as described in "M13 Cloning/Dideoxy Sequencing Instruction Manual" (BRL).

(h) DNA sequence analysis

Single-stranded phage DNA was isolated from 6 hour 1.5 ml of liquid culture as described in "M13 Cloning/Dideoxy Sequencing Instruction Manual" (BRL) and was sequenced directly by the dideoxy-nucleotide method using Klenow Fragment, DNA Polymerase with the M13-primer SEQ ID NO: 4: 5'-CCCAGTCACGACGTTGT-3'. Annealing reaction mixture containing 1.5 to 2.0 μg of the single-stranded DNA, 3 μl (5×) of sequencing buffer and 1 μl primer in a total volume of 15 μl was heated at 95°–100° C. for 5 min and the mixture was left to cool in the heating block to room temperature about 45 min, and briefly microfuged. To 15 μl annealed/primer mixture, 1 μl 0.1M DTT, 1 μl of $^{35}$S dATP (Amersham) and one unit Klenow Fragment Polymerase (DuPont) were added and tubes incubated for 3 min at room temperature. This mixture was dispensed into four tubes containing 2 μl 0.1 mM dNTPs and ddNTPs sequencing mixtures. The tubes were incubated for 30 min at 37° C., then briefly microfuged and 2 μl of 0.4 mM of sequence mixture, without ddNTPs, but which also contained unlabelled dATP, was added to each tube. After a further 20 min incubation at 37° C., 5 μl of stop solution was added to each tube and mixed by centrifugation. Samples were run in 6% acrylamide gel containing 7M Urea in Tris-borate electrophoresis (TBE) buffer at 60 watts (40 mA). Samples were boiled for 5 min and cooled on wet ice before loading.

One sample from a clone designated "Nar 50" was also sequenced by the automated processes of the Model 370A DNA sequencer (Applied Bios) at University of Durham (England) with dye Primer [−21M13]. Nucleotide sequencing data was compared with the GenBank database by a computer program.

(i) Amplification of clones by the PCR

Clones of M13 double stranded DNA and single-stranded DNA with the insert were used for amplification by polymerase chain reaction (PCR) with −20 and reverse primer of M3. Reactions were carried out in a 100 μl reaction mixture in a Perkin Elmer Cetus PCR kit according to manufacturer's instructions. Forty cycles of PCR were carried out on all samples as follows: denaturation for 60 s at 94° C., annealing of primers for 150 s at 45° C. and extension for 120 s at 75° C. PCR products were analysed on 1.0% agarose gel with ethidium bromide staining.

RESULTS

Analysis of nucleic acid fraction of both scrapie-infected brain and the equivalent fraction of uninfected brain isolated and run in neutral agarose gel with TAE buffer revealed significant differences between scrapie-infected and uninfected samples, as described in detail by H. K. Narang, N. S. Millar, D. M. Asher and D. C. Gajdusek, Intervirology 1991, 32, 316–324 (1991). Briefly, in both samples a band was present corresponding in size to that of hamster mitochondrial (mr) DNA, a double stranded circular molecule of approximately 15.7 kb. In addition to this band, several broad bands of high molecular weight were seen only in the scrapie-infected sample. In the said previous study it was shown that the slower migrating bands of nucleic acid were multimeric forms of circular mtDNA.

Analysis of nucleic acid fraction of scrapie-infected brain and the equivalent fraction of uninfected brain, isolated and run in the alkaline agarose gel with NaOH stained with ethidium bromide, revealed that one band of about 1.2 kb remained visible under the alkaline conditions in the lane with scrapie-infected brain, while no DNA markers were seen (these having been denatured under the alkaline conditions). All these nucleic acid bands were visualised after the gel was neutralised with NaCl and Tris buffer.

The 1.2 kb scrapie-specific band was excised, and synthesised into double strand of cDNA as described in Methods. Three clones with inserts at the SmaI cut site were investigated. One had an insert of only 13 bases, SEQ ID NO: 5: 1 ATATATATAC GTA 13.

The other two sequences read (TACGTA)$_n$ TA and both were difficult to read after 38 bases. One of the two clones "Nar 50" (with 38 base reading) was also sequenced by the automated system and results were found to be the same. The reading sequence of six bases TACGTA was repeated over and over again in the same order.

There is a restriction site for SnaB1 cutting TACGTA in the middle. There is also a single site in M13 for SnaB1 restriction enzyme. The double stranded DNA of M13 plasmid with the insert was prepared from *E. coli* by a small-scale preparation method. The DNA was cut with the SnaB1 restriction enzyme. Gel analysis revealed two bands one containing over 5,000 base and the other about 2,250 bases. Because of the large size of the two fragments produced, it was difficult to estimate the size of the insert in them.

Analysis of 10 μl of the amplified PCR product of M13 double stranded DNA and single-stranded DNA run in the neutral agarose gel with TAE buffer revealed amplification of a single band of about 250 bases. By calculating the bases of M13 including the primers at about 100 bases, an insert of size of about 150 bases was indicated. The PCR product was cut with EcoR1, HindIII, SnaB1 or a combination of two enzymes or all three. EcoR1 or HindIII made very little difference to the mobility of the band but SnaB1 by itself or in combination with the other two restriction enzymes reduced its size by about half to 125 bases.

Comparison of the nucleotide sequence of the inserted DNA to the GenBank nucleotide database revealed no significant homology.

When repeating the preparative procedure of Example 1, a further sequence, ATAATA, preceding the palindromic sequence TAGCTA, was detected. This is believed to be at least part of an intermediate (linker) sequence connecting palindromic sequences.

EXAMPLE 2

This Example illustrates a method of diagnostic assay using the PCR.

The scrapie etc. level in the blood would be $10^3$ doses of infectivity per gram (or cm.$^3$) of blood. (A dose of infectivity is that which when diluted and inoculated into mice gives diseases in 50% of the mice). This level is about constant in the blood. As little as 1 microliter of blood is likely to contain one molecule of the DNA, which is all that is needed for the PCR, but in practice one would use a much larger sample. The blood is treated with proteinase K to remove unwanted proteins from association with the DNA and heated to destroy proteinase K at 95° C. for 10 minutes. The PCR is performed using a (TACGTA)$_3$ primer, mixed nucleotides in Taq polymerase for 40 cycles. The PCR product is then run on a gel in 10 μl samples. The first cycle of the three steps of annealing with primer, extension and denaturation is carried out at 95° C. throughout. Thereafter 40 cycles are carried out at 45°–50° C., 72° C. and 92° C. in the three steps.

One sample of PCR product is digested with the restriction enzyme SnaBI, another is left untreated. Where the band due to the PCR product disappears on treatment with the enzyme, the scrapie-specific DNA is present. (The effect of SnaB1 is to cut the TACGTA sequence, forming many small pieces of DNA).

The following Sequence Listing has been prepared by use of the "Patentin" program supplied by the United States Patent Office. The program contains an error which causes nucleotide lengths to be expressed in "base pairs" even when the nucleic acid is single-stranded, as here. For "base pairs" read "nucleotides".

I claim:

1. Oligonucleotides having a length of 16 to 200 nucleotides, of formula $$(X)_a\text{-}(6N\text{-palindrome})_n\text{-}(Y)_b \quad (1)$$

wherein:

"6N-palindrome" represents TACGTA, ACGTAT, CGTATA, GTATAC, TATACG or ATACGT, read in the conventional notation with the 5'-end at the left;

"n" is an integer of at least 2;

X is 5'-end DNA and "a" is 0 or 1; and

Y is 3'-end DNA and "b" is 0 or 1;

provided that when n is 2, either (1) "a" is 1 and X comprises at least the last four nucleotides of TACGTA, ACGTAT, CGTATA, GTATAC, TATACG or ATACGT respectively, immediately to the 5'-end of the respective 6N-palindrome sequence or (2) "b" is 1 and Y comprises at least the first four nucleotides of TACGTA, ACGTAT, CGTATA, GTATAC, TATACG or ATACGT respectively, immediately to the 3'-end of said respective "6N-palindrome" sequence, or any labeled form thereof.

2. Oligonucleotides according to claim 1, wherein "n" is from 2 to 6.

3. Oligonucleotides according to claim 1, wherein:

"a" is 0 or X represents a residue of said 6N-palindrome sequence and "a" is 1,

"b" is 0 or Y represents a residue of said 6N-palindrome sequence and "b" is 1, and the total length of palindromic sequence within the oligonucleotide is from 16 to 24.

4. Oligonucleotides according to claim 1, wherein "n" is from 2 to 4.

5. Oligonucleotides according to claim 1, wherein "6N-palindrome" represents TACGTA, "a" is 1 and X comprises a sequence of formula (A)p(TA)q where "p" is 0 or 1 and "q" is from 1 to 20, immediately to the 5'-end of the "6N-palindro" sequence.

6. Oligonucleotides according to claim 1, of length 16 to 45 nucleotides.

7. Oligonucleotides according to claim 1, in a labeled form wherein the label is attached to the 5'-end.

8. A kit for carrying out a polymerase chain reaction, the kit comprising:

(1) deoxyribonucleotides;

(2) a polymerase suitable for the polymerase chain reaction; and (3) at least one oligonucleotide primer having a length of 12 to 200 nucleotides, of formula $$(X)_1\text{-}(6N\text{-palindrome})_n\text{-}(Y)_b \quad (1)$$

wherein:

"6N-palindrome" represents TACGTA, ACGTAT, CGTATA, GTATAC, TATACG or ATACGT, read in the conventional notation with the 5'-end at the left;

"n" is an integer of at least 2;

X is 5'-end DNA and "a" is 0 or 1; and

Y is 3'-end DNA and "b" is 0 or 1;

or any labeled form thereof.

9. A kit according to claim 8, wherein component (3) comprises forward and reverse primers of a said oligonucleotide.

10. A kit according to claim 8, wherein the oligonucleotide is unlabeled.

11. A kit according to claim 8, which further comprises a restriction enzyme capable of restricting the 6N-palindrome.

12. A kit according to claim 8, wherein the restriction enzyme is SnaBI, AccI, MaeI or SnaI.

13. A kit according to claim 8, wherein n is from 2 to 6.

14. A kit according to claim 8, wherein n is from 2 to 4.

15. A kit according to claim 8, wherein the oligonucleotide is of length 16 to 45 nucleotides.

16. A method of detecting or estimating the amount of DNA specific for an encephalopathy implicating prions, said DNA being suspected of being present in a sample, which comprises treating said sample to amplify the DNA, using as a primer for the amplification at least one oligonucleotide primer having a length of 12 to 200 nucleotides, of formula

wherein:

"6N-palindrome" represents TACGTA, ACGTAT, CGTATA, GTATAC, TATACG or ATACGT, read in the conventional notation with the 5'-end at the left;

"n" is an integer of at least 2;

X is 5'-end DNA and "a" is 0 or 1; and

Y is 3'-end DNA and "b" is 0 or 1;

or any labeled form thereof, detecting the product of the amplification, analyzing the product for the presence of at least two tandem repeats of a TACGTA, ACGTAT, CGTATA, GTATAC, TATACG or ATACGT sequence, said sequence being read with the 5'-end at the left, and from said analysis detecting the presence or estimating the amount of said encephalopathy-specific DNA in the sample.

17. A method according to claim 16, wherein the DNA is amplified by a polymerase chain reaction.

18. A method according to claim 16, wherein the product of the amplification is restricted enzymically and the restricted product is compared with the unrestricted product, whereby disappearance of longer lengths of DNA upon restriction indicates presence of the encephalopathy-specific DNA.

19. A method according to claim 42, wherein the restriction enzyme is SnaBI, AccI, MaeI or SnaI.

20. A method according to claim 16, wherein n is from 2 to 6.

21. A method according to claim 16, wherein n is from 2 to 4.

22. A method according to claim 16, wherein the oligonucleotide is of length 16 to 45 nucleotides.

23. Scrapie-specific DNA which comprises at least one sequence of formula $(TACGTA)_n$ where n is at least 6.

24. DNA according to claim 23, which comprises at least one SEQ ID. NO: 5 sequence.

25. A method of detecting or estimating the amount of DNA specific for an encephalopathy implicating prions, said DNA being suspected of being present in a sample, which comprises probing said sample with a labeled oligonucleotide probe DNA having a length of 12 to 200 nucleotides, of formula

wherein:

"6N-palindrome" represents TACGTA, ACGTAT, CGTATA, GTATAC, TATACG or ATACGT, read in the conventional notation with the 5'-end at the left;

"n" is an integer of at least 2;

X is 5'-end DNA and "a" is 0 or 1; and

Y is 3'-end DNA and "b" is 0 or 1;

under hybridization conditions and detecting or estimating the presence or amount of hybridization, and thereby the presence or amount of said encephalopathy—specific DNA in the sample.

26. A method according to claim 25, wherein the sample is treated to amplify the DNA prior to said probing.

27. A method according to claim 25, wherein when n is 2, "b" is 1 and Y represents at least the first four nucleotides of TACGTA, ACGTAT, CGTATA, GTATAC, TATACG or ATACGT respectively, immediately to the 3'-end of the respective "6N-palindrome" sequence.

28. A method according to claim 25, wherein n is from 2 to 6.

29. A method according to claim 25, wherein n is from 2 to 4.

30. A method according to claim 25, wherein the oligonucleotide is of length 16 to 45 nucleotides.

31. A primer for DNA amplification comprising an oligonucleotide claimed in claim 1.

32. A probe comprising an oligonucleotide claimed in claim 1 in labeled form.

33. Oligonucleotides having a length of 16 to 200 nucleotides, of formula

wherein:

"6N-palindrome" represents TACGTA, ACGTAT, CGTATA, GTATAC, TATACG or ATACGT, read in the conventional notation with the 5'-end at the left;

"n" is an integer of 2 to 6;

X is 5'-end DNA and "a" is 0 or 1; and

Y is 3'-end DNA and "b" is 0 or 1;

provided that when n is 2, either (1) "a" is 1 and X comprises at least the last four nucleotides of TACGTA, ACGTAT, CGTATA, GTATAC, TATACG or ATACGT respectively, immediately to the 5'-end of the respective 6N-palindrome sequence or (2) "b" is 1 and Y comprises at least the first four nucleotides of TACGTA, ACGTAT, CGTATA, GTATAC, TATACG or ATACGT respectively, immediately to the 3'-end of said respective "6N-palindrome" sequence, or any labeled form thereof.

34. Oligonucleotides according to claim 33, wherein:

"a" is 0 or X represents a residue of said 6N-palindrome sequence and "a" is 1,

"b" is 0 or Y represents a residue of said 6N-palindrome sequence and "b" is 1, and the total length of palindromic sequence within the oligonucleotide is from 16 to 24.

35. Oligonucleotides according to claim 33, wherein "n" is from 2 to 4.

36. Oligonucleotides according to claim 33, wherein "6N-palindrome" represents TACGTA, "a" is 1 and X comprises a sequence of formula (A)p(TA)q where "p" is 0 or 1 and "q" is from 1 to 20, immediately to the 5'-end of the "6N-palindro" sequence.

37. Oligonucleotides according to claim 33, of length 16 to 45 nucleotides.

38. Oligonucleotides according to claim 33, in a labeled form wherein the label is attached to the 5'-end.

39. A kit for carrying out a polymerase chain reaction, the kit comprising:

(1) deoxyribonucleotides;

(2) a polymerase suitable for the polymerase chain reaction; and (3) at least one oligonucleotide primer having a length of 12 to 200 nucleotides, of formula $(X)_a\text{-}(6N\text{-palindrome})_n\text{-}(Y)_b$            (1)

wherein:

"6N-palindrome" represents TACGTA, ACGTAT, CGTATA, GTATAC, TATACG or ATACGT, read in the conventional notation with the 5'-end at the left;

"n" is an integer of 2 to 6;

X is 5'-end DNA and "a" is 0 or 1; and

Y is 3'-end DNA and "b" is 0 or 1;

or any labeled form thereof.

40. A kit according to claim 39, wherein component (3) comprises forward and reverse primers of a said oligonucleotide.

41. A kit according to claim 39, wherein the oligonucleotide is unlabeled.

42. A kit according to claim 39, which further comprises a restriction enzyme capable of restricting the 6N-palindrome.

43. A kit according to claim 39, wherein the restriction enzyme is SnaBI, AccI, MaeI or SnaI.

44. A kit according to claim 39, wherein n is from 2 to 4.

45. A kit according to claim 39, wherein the oligonucleotide is of length 16 to 45 nucleotides.

46. A method of detecting or estimating the amount of DNA specific for an encephalopathy implicating prions, said DNA being suspected of being present in a sample, which comprises treating said sample to amplify the DNA, using as a primer for the amplification at least one oligonucleotide primer having a length of 12 to 200 nucleotides, of formula $(X)_a\text{-}(6N\text{-palindrome})_n\text{-}(Y)_b$            (1)

wherein:

"6N-palindrome" represents TACGTA, ACGTAT, CGTATA, GTATAC, TATACG or ATACGT, read in the conventional notation with the 5'-end at the left;

"n" is an integer of 2 to 6;

X is 5'-end DNA and "a" is 0 or 1; and

Y is 3'-end DNA and "b" is 0 or 1;

or any labeled form thereof, detecting the product of the amplification, analyzing the product for the presence of at least two tandem repeats of a TACGTA, ACGTAT, CGTATA, GTATAC, TATACG or ATACGT sequence, said sequence being read with the 5'-end at the left, and from said analysis detecting the presence or estimating the amount of said encephalopathy-specific DNA in the sample.

47. A method according to claim 46, wherein the DNA is amplified by a polymerase chain reaction.

48. A method according to claim 46, wherein the product of the amplification is restricted enzymically and the restricted product is compared with the unrestricted product, whereby disappearance of longer lengths of DNA upon restriction indicates presence of the encephalopathy-specific DNA.

49. A method according to claim 48, wherein the restriction enzyme is SnaBI, AccI, MaeI or SnaI.

50. A method according to claim 46, wherein n is from 2 to 4.

51. A method according to claim 47, wherein the oligonucleotide is of length 16 to 45 nucleotides.

52. A method of detecting or estimating the amount of DNA specific for an encephalopathy implicating prions, said DNA being suspected of being present in a sample, which comprises probing said sample with a labeled oligonucleotide probe DNA having a length of 12 to 200 nucleotides, of formula $(X)_a\text{-}(6N\text{-palindrome})_n\text{-}(Y)_b$            (I)

wherein:

"6N-palindrome" represents TACGTA, ACGTAT, CGTATA, GTATAC, TATACG or ATACGT, read in the conventional notation with the 5'-end at the left;

"n" is an integer of 2 to 6;

X is 5'-end DNA and "a" is 0 or 1; and

Y is 3'-end DNA and "b" is 0 or 1;

under hybridization conditions and detecting or estimating the presence or amount of hybridization, and thereby the presence or amount of said encephalopathy specific DNA in the sample.

53. A method according to claim 52, wherein the sample is treated to amplify the DNA prior to said probing.

54. A method according to claim 52, wherein when n is 2, "b" is 1 and Y represents at least the first four nucleotides of TACGTA, ACGTAT, CGTATA, GTATAC, TATACG or ATACGT respectively, immediately to the 3'-end of the respective "6N-palindrome" sequence.

55. A method according to claim 52, wherein n is from 2 to 4.

56. A method according to claim 52, wherein the oligonucleotide is of length 16 to 45 nucleotides.

57. A primer for DNA amplification comprising an oligonucleotide claimed in claim 33.

58. A probe comprising an oligonucleotide claimed in claim 33 in labeled form.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: satellite
  ( B ) LOCATION: 1..6
  ( D ) OTHER INFORMATION: /rpt_type= "tandem"

( x i ) SEQUENCE DESCRIPTION: SEQ ID NO:1:

TACGTATACG TA      12

( 2 ) INFORMATION FOR SEQ ID NO:2:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: satellite
  ( B ) LOCATION: 6..12
  ( D ) OTHER INFORMATION: /rpt_type= "tandem"

( x i ) SEQUENCE DESCRIPTION: SEQ ID NO:2:

ATACGTATAC GTATACG      17

( 2 ) INFORMATION FOR SEQ ID NO:3:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: satellite
  ( B ) LOCATION: 1..6
  ( D ) OTHER INFORMATION: /rpt_type= "tandem"

( x i ) SEQUENCE DESCRIPTION: SEQ ID NO:3:

TATACGTATA CGTATACH      18

( 2 ) INFORMATION FOR SEQ ID NO:4:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: M13 primer ( x i ) SEQUENCE DESCRIPTION: SEQ ID NO:4:

CCCAGTCACG ACGTTGT                                                                                          17

( 2 ) INFORMATION FOR SEQ ID NO:5:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

ATATATATAC GTA                                                                                              13